United States Patent [19]

Breccia et al.

[11] Patent Number: 4,767,758

[45] Date of Patent: Aug. 30, 1988

[54] PHARMACEUTICAL COMPOSITIONS CONTAINING THIOPHENE COMPOUNDS, AND NEW THIOPHENE COMPOUNDS

[75] Inventors: Alberto Breccia; Adamo Fini, both of Bologna, Italy

[73] Assignee: Consiglio Nazionale Delle Ricerche, Rome, Italy

[21] Appl. No.: 20,162

[22] Filed: Feb. 26, 1987

Related U.S. Application Data

[63] Continuation of Ser. No. 813,787, Dec. 27, 1985, abandoned.

[30] Foreign Application Priority Data

Dec. 28, 1984 [IT] Italy .................. 24283 A/84

[51] Int. Cl.⁴ ................. A61K 31/38; A61K 31/45
[52] U.S. Cl. ..................... 514/231.5; 514/2;
  514/23; 514/42; 514/252; 514/397; 514/438;
  514/444; 514/445; 514/447; 514/448;
  514/230.8; 514/232.2
[58] Field of Search ............ 514/445, 447, 448, 438,
  514/230, 252, 2, 23, 42, 444, 397

[56] References Cited

U.S. PATENT DOCUMENTS

3,639,613  2/1972  Dunn et al. .................. 514/447

FOREIGN PATENT DOCUMENTS

0186252  7/1986  European Pat. Off. ............ 514/447

OTHER PUBLICATIONS

Hartough Thiophene & Its Deriv. (1952), pp. 182, 184, 190, 192, 208, 213, 218, 229, 231, 237, 291, 303, 319, 320, 373, 378–381.

*Primary Examiner*—Alan Siegel
*Attorney, Agent, or Firm*—Stevens, Davis, Miller & Mosher

[57] ABSTRACT

A pharmaceutical composition containing a thiophene compound of formula:

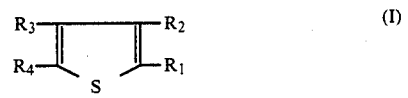

where $R_1$, $R_2$, $R_3$ and $R_4$ have the meanings given in the description, or a pharmaceutically acceptable addition salt thereof.

Said pharmaceutical compositions are useful in treating tumors.

New thiophene compounds are also described.

4 Claims, No Drawings

PHARMACEUTICAL COMPOSITIONS CONTAINING THIOPHENE COMPOUNDS, AND NEW THIOPHENE COMPOUNDS

This application is a continuation of application Ser. No. 813,787, filed Dec. 27, 1985, now abandoned.

This invention relates to a pharmaceutical composition containing a thiophene compound of formula:

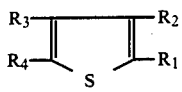

wherein $R_1$ is hydrogen, p-nitrophenoxy, halogen, carboxy, $CON(R_5,R_6)$, $CONH(CHR_9)_n$—COOH, $CH_2NHR_8$, $NH(CHR_9)_nAR_{10}$, CH=NOH, $NO_2$, CHO, $OR_7$ and where in turn $R_5$ and $R_6$, the same or different, are hydrogen, a straight or branched alkyl having 1-8C atoms, a heterocyclic ring selected from the group comprising thiophene and imidazole, ascorbyl, peptidyl having up to 5 amino acids or a sugar radical; or $R_5$ and $R_6$ together with the nitrogen atom to which they are linked form the groups necessary for completing a 5-membered heterocyclic ring which may contain other heteroatoms selected from the group consisting of O and N; $R_7$ has the meanings indicated above for $R_5$ and $R_6$; $R_8$ is an acyl of an aliphatic carboxylic acid having 1-4C atoms, $R_9$ is hydrogen or methyl; $R_{10}$ is methyl or phenyl; n is 1,2,3 or 4; and A is CO or $SO_2$;

$R_2$ is hydrogen, $NO_2$, halogen, $CH(COOH)_2$, OH, $(CH_2)_nCOOH$ where in turn n is 0,1,2,3 or 4;

$R_3$ is hydrogen, $NO_2$, OH;

$R_4$ is hydrogen, $NO_2$, halogen, $SO_2CH_3$, OH, $N(R_5, R_6)$ where in turn $R_5$ and $R_6$ have the meanings indicated above, provided however that at least two of the substituents $R_1$, $R_2$, $R_3$ and $R_4$ are not hydrogen;

or a pharmaceutically acceptable addition salt thereof with pharmaceutically acceptable bases or acids.

In the preferred compounds $R_1$ is H, bromine, iodine, carboxy, p-nitrophenoxy, $CON(R_5,R_6)$, $CONH(CHR_9)_n$—COOH, $NH(CHR_9)_nAR_{10}$, CH=NOH where in turn $R_5$ and $R_6$, the same or different, are hydrogen, a straight or branched alkyl having 1-3C atoms, or together with the nitrogen atom to which they are linked, are the groups necessary to complete a morpholine or a piperazine ring; $R_9$ is hydrogen or methyl; $R_{10}$ is methyl or phenyl; n is 1, 2 or 3; and A is CO or $SO_2$;

$R_2$ is hydrogen, nitro, carboxy or $CH(COOH)_2$;

$R_3$ is hydrogen or nitro; and $R_4$ is hydrogen, bromine, iodine, nitro or $SO_2$-$CH_3$.

Some compounds of formula I are new and they are another object of this invention.

More particularly are new the compounds of formula I wherein $R_1$ is not H when $R_2$ and $R_4$ are $NO_2$, and $R_3$ is H;

$R_1$ is not iodine when $R_2$ is $NO_2$, $R_3$ is H and $R_4$ is $NO_2$ or $CH_3SO_2$;

$R_1$ is not p-nitrophenoxy when $R_2$ is $NO_2$ and both $R_3$ and $R_4$ are H; and $R_1$ is not $CONH_2$ or COOH when $R_4$ is $NO_2$ and both $R_2$ and $R_3$ are H.

The pharmacological action of the compounds of formula I is performed through inhibition of neoplastic growth of cells, blocking of reactions of radical oxygen, and radiosensitization. Said compounds are thus particularly useful in tumor therapy.

The compounds of this invention may be prepared according to conventional techniques.

Preparation of the compounds of formula I in which $R_1$ is iodine, $R_2$ is $NO_2$, $R_3$ is H, and $R_4$ is $NO_2$ (Compound 1);

$R_1$ is H, $R_2$ is $NO_2$, $R_3$ is H, and $R_4$ is $NO_2$ (Compound 2);

$R_1$ is iodine, $R_2$ is $NO_2$, $R_3$ is H, and $R_4$ is $CH_3SO_2$ (Compound 3);

$R_1$ is p-nitro-phenoxy, $R_2$ is $NO_2$, both $R_3$ and $R_4$ are H (Compound 4);

$R_1$ is $CONH_2$, both $R_2$ and $R_3$ are H, $R_4$ is $NO_2$ (Compound 5);

$R_1$ is COOH, both $R_2$ and $R_3$ are H, $R_4$ is $NO_2$ (Compound 6), was described by D. Spinelli et al., J.C.S. Perkin Trans, 2,747 1976 C; J.C.S. Perkin II, 1972.

Examples of conventional techniques for preparing new compounds of formula I are nitration and halogenation of the thiophene ring, preparation of reactive derivatives of the carboxylic function, such as acid chloride, and use thereof to prepare the amides.

Nitration is preferably performed by suspending the proper thiophene derivative in acetic anhydride and adding fuming nitric acid. The reaction mixture is then poured into cold water or water and ice and the desired product is separated by conventional techniques such as filtration or extraction with suitable solvents, e.g. ethyl ether.

Examples of conventional techniques for preparing halo-thiophene derivatives are the treatment of the proper thiophene derivative (a) with a solution of a halogen, e.g. chlorine or bromine, in acetic acid, or (b) with sulfuryl chloride in carbon tetrachloride in the presence of a suitable catalyst such as stannous chloride.

The preparation of reactive derivatives of the carboxylic function such as the acyl chlorides may be also performed by conventional techniques such as treatment with thionyl chloride or phosphorus pentachloride.

The acyl halides may be then reacted in a conventional manner with ammonia, primary or secondary amines, alcohols, phenols, sugars, hydrazines and the like to afford amides, esters or hydrazides.

According to their very nature the compounds of formula I can form addition salts with pharmaceutically acceptable inorganic or organic bases or acids, and these salts are another object of this invention.

The biological and pharmacological activity of the compounds under examination was tested on cell cultures and under gamma radiations. Concentrations of $10^{-6}$, $5 \times 10^{-6}$, $10^{-5}$ and $10^{-3}$M of each compound were used. These aqueous solutions were added to cell cultures containing from 50 to 60 L 929 cells per $mm^2$; nutrient solution RPM-1-1640 containing 3% calf serum. Contact between the cells and the compound under examination was continued for six hours under nitrogen and under air. Parts of the solutions during the contact with the drug were irradiated in gamma cell with 1000, 2000 and 3000 rad always using a control sample without the drug.

The results obtained are given in Table 2 (cytotoxicity) and in Table 1 (radiosensitization of the cells in hypoxic condition, in comparison with Misonidazole, a drug known as a radiosensitizer).

For testing the reactivity with oxygen radicals, solutions of the compounds under examination in very pure water were submitted to irradiation by an electron flow in accordance with the following procedure:

(a) Reactivity with OH radicals

The irradiated solution for measurement of reactivity with OH radicals contained KCNS $10^{-4}$M and increasing concentrations of the compounds under examination. The concentrations were $10^{-6}$ and $6\times10^{-6}$ for the first five compounds of Table 1, $10^{-5}$ and $10^{-4}$, $10^{-3}$M for the other eight compounds.

The water used for the tests was neutral and made absolutely pure by deionization and four distillations also in the presence of oxidizing agents ($KMnO_4$).

The irradiation conditions were: pulse 50 nsec, dose 18 Gy.

Absorption was performed at $\lambda = 500$ nm. The results are given in Table 3.

(b) Reactivity with $O_2$ radicals

The $O_2$ species was generated by irradiation of a $5\times10^2$M solution of potassium formiate satured with $O_2$ with 12 MeV pulsed electron beams.

The concentration of the $O_2$ radical produced is depending from the irradiation dose (which is proportional to the length of the pulse) and was in any case in excess with respect to the concentration of the reacting substance.

The results are given in Table 3.

TABLE 1

| Compound | Radiosensitization Index (R.S.I) | |
|---|---|---|
|   | Concentration | R.S.I. |
| 1 | $0.5 \times 10^{-5}$ M | 1.55 |
| 2 | " | 1.38 |
| 3 | " | 1.30 |
| 4 | " | 1.80 |
| 5 | $5 \times 10^{-5}$ M | 1.40 |
| 6 | $1 \times 10^{-4}$ M | 1.82 |
| 7 | " | 1.38 |
| 8 | " | 1.30 |
| 9 | " | 1.56 |
| 10 | " | 1.58 |
| 11 | " | 1.65 |
| 12 | " | 1.88 |
| 13 | " | 1.65 |
| Misonidazole | $1 \times 10^{-3}$ M | 1.65 |

TABLE 2

Cytotoxicity Index

| Compound | Concentration of the compound: $10^{-5}$ M | Culture time | | | |
|---|---|---|---|---|---|
| | | 0 hr | 6 hr | 12 hr | 24 hr) |
| | | Control (number of cells) | | | |
| | | 40 | 62 | 80 | 166 |
| 1 | 0.5 | 36 | 35 | 42 | 71 |
| 2 | 0.5 | 46 | 40 | 68 | 80 |
| 3 | 0.5 | 37 | 30 | 35 | 50 |
| 4 | 0.5 | 56 | 34 | 48 | 70 |
| 5 | 5 | 40 | 32 | 50 | 80 |
| 6 | 5 | 50 | 60 | 70 | 110 |
| 7 | 5 | 56 | 70 | 75 | 164 |
| 8 | 5 | 47 | 50 | 80 | 152 |
| 9 | 5 | 64 | 60 | 80 | 138 |
| 10 | 5 | 50 | 52 | 60 | 86 |
| 11 | 5 | 44 | 52 | 60 | 90 |
| 12 | 5 | 50 | 60 | 74 | 136 |
| 13 | 5 | 43 | 50 | 70 | 130 |

TABLE 3

Reactivity with OH and $O_2$ radicals measured as a speed constant

| Compound | $K_{OH} \cdot (M^{-1} sec^{-1})$ | $K_{O_2-} \cdot (M^{-1} sec^{-1})$ |
|---|---|---|
| 1 | $2.1 \times 10^{10}$ | $3.5 \times 10^6$ |
| 4 | $1.3 \times 10^{10}$ | $2.0 \times 10^4$ |
| 5 | $2.3 \times 10^{10}$ | $3.0 \times 10^4$ |
| 6 | $7.5 \times 10^9$ | $1.0 \times 10^5$ |
| 9 | $3.1 \times 10^{10}$ | $2.3 \times 10^5$ |
| 10 | $1 \times 10^{10}$ | $3.3 \times 10^4$ |
| 12 | $7.2 \times 10^9$ | $1.0 \times 10^4$ |
| 13 | $8.0 \times 10^9$ | $2.3 \times 10^4$ |

The acute toxicity test was carried out by oral and intravenous route on male mice, weighing 19–21 g, which were deprived of meal for 16 hrs before treatment. Oral administration was performed by a gastric probe at doses of 500, 750, 1000 and 2000 mg/kg respectively, of the compounds under examination in aqueous solution of Tween (R). The intravenous administrations was performed in the caudal vein at doses of 100 and 200 mg/kg in 0.9% sodium chloride solution. The administered volumes were 1 ml/20 g by oral route and 0.5 ml/20 g by intravenous route.

After administration the mice were kept under control for 14 days.

The results are given in Table 4.

When occured, the death of the mice receiving the compounds by oral route happened from 4 to 24 hrs after administration and was preceded by trembles, fits and dyspnea. The animals which survived did not show any pathological symptom.

No death occured after intravenous administration.

For therapeutical purposes the compounds of formula I or their salts with pharmaceutically acceptable bases or acid will be administered in vivo in dosages sufficient to reach the desired pharmacological effect. Said quantities will depend on the type of disease to be treated, the patient's condition and weight, the administration route, and other parameters known to the artisan.

TABLE 4

LD$_{50}$ of Compounds 1, 9, 12 and 13

| ROUTE | Dose (mg/kg) | | | | Nos. of animals | | | | Death | | | | LD$_{50}$ (mg/kg) | | | |
|---|---|---|---|---|---|---|---|---|---|---|---|---|---|---|---|---|
| | 1 | 12 | 13 | 9 | 1 | 12 | 13 | 9 | 1 | 12 | 13 | 9 | 1 | 12 | 13 | 9 |
| ORAL | — | 2000 | 2000 | 2000 | — | 5 | 5 | 5 | — | 5/5 | 3/5 | 3/5 | 760 | 1200 | 1800 | 2000 |
| | 1000 | 1000 | 1000 | 1000 | 5 | 5 | 5 | 5 | 5/5 | 2/5 | 2/5 | 1/5 | | | | |
| | 750 | 750 | 750 | 750 | 5 | 5 | 5 | 5 | 2/5 | 0/5 | 0/5 | 0/5 | | | | |
| | 500 | 500 | 500 | 500 | 5 | 5 | 5 | 5 | 0/5 | 0/5 | 0/5 | 0/5 | | | | |
| INTRAVENOUS | 200 | 200 | 200 | 200 | 5 | 5 | 5 | 5 | 0/5 | 0/5 | 0/5 | 0/5 | | | | |
| | | | | | | | | | | | | | 200 | | | |
| | 100 | 100 | 100 | 100 | 5 | 5 | 5 | 5 | 0/5 | 0/5 | 0/5 | 0/5 | | | | |

Generally the dose shall be comprised from 1 to 500 mg/kg/day preferably from 1 to 100 mg/kg/day.

The compounds of formula I or their salts with pharmaceutically acceptable bases or acids will be preferably administered in finished pharmaceutical forms by parental or injectable route.

Examples of suitable pharmaceutical forms for oral administration are tablets, capsules, pills, syrups and solutions.

For parenteral administration sterile and lyophilized solutions are preferred.

Together with the active ingredient, i.e. a compound of formula I or a salts thereof with pharmaceutically acceptable bases or acids, the pharmaceutical forms may also contain suitable inert and nontoxic solid and liquid diluents as well as preservatives, stabilizing, moistening and emulsifying agents, salts to regulare osmotic pressure, buffers, dye, flavouring agents, and the like.

They may be prepared by known techniques and may also contain other active ingredients.

The following examples are intended to illustrate the invention without however limiting it.

EXAMPLE 1

(a) 5-nitro-2-thiphenecarboxylic acid 2-thiophenecarboxylic acid (12.8 g; 0.1 mol) is suspended in 30 ml of acetic anhydride; to the mixture thus obtained cooled to 10° C. and stirred vigourously are added slowly 9 ml of fuming nitric acid (d=1.49 g/ml). At the end the mixture appears homogeneous. It is poured into water and ice, extracted with ethyl ether and dried; the solvent is removed by evaporation. Yield, 70% after separation of the 4-nitro-2-thiophenecarboxylic acid analog owing to the different solubility in water of their barium salts; m.p. 157°-158° C.

5-nitro-3-thiophenecarboxylic acid, m.p. 146° C., is prepared in a similar manner.

(b) 4-nitro-2-cyanothiophene

To a solution of 2-cyanothiophene (10.9 g; 0.1 mol) in 25 ml of acetic anhydride (t=10° C.) are added 9 ml of fuming nitric acid (d=1.49 g/ml).

The temperature is kept under control. When the reaction is complete the reaction mixture is poured into ice, the precipitate is filtered, dried, dissolved in 40 ml of ethyl alcohol, and crystallized up to constant melting point (102° C.); Yield, 30%.

(c) 4-nitrio-2-thiophenecarboxylic acid

A mixture of 4-nitro-2-cyanothiophene (1.5 g; 0.1 mol) in 20 ml of concentrate hydrochloric acid is heated for two hours. As hydrolysis proceeds the reactant goes into solution. The desired product precipitates from the reaction mixture by cooling; m.p. 152°-154° C. (water).

(d) 5-bromo-3-thiophenecarboxylic acid

A solution containing 16 g of $Br_2$ (0.1 mol) in glacial acetic acid (200 ml) is added slowly to a solution of 3-thiophenecarboxylic acid (12.8 g; 0.1 mol) in 100 ml of glacial acetic acid.

The mixture is stirred for 20' and then poured into water and ice.

The white precipitate is filtered, washed and crystallized from water. Yield, 70%.

(e) 5-nitro-2-thiophenecarboxylic acid chloride

The crystallized acid (1.7 g; 0.01 mol) is refluxed with an excess of thionyl chloride (0.2 mol) for 60'. The excess of thionyl chloride is removed under vacuum; after distillation in vacuum the desired product solidifies slowly.

5-bromo-3-thiophenecarboxylic acid chloride and its analogs are prepared in a similar manner.

EXAMPLE 2

5-nitro-2-thiophenecarboxylic acid amides 5-nitro-2-thiophenecarboxylic acid chloride is dissolved in toluene and treated with a 4% aqueous solution of sodium hydroxide containing an equimolecular quantity of the desired amino acid or amine.

The two phases are separated and the product is obtained by acidification of the aqueous phase. Alternatively when the desired product is poorly soluble in water, it is recovered from the organic phase.

The nitrothienylamides may also be obtained by nitration of the amides.

In this manner were prepared
N-(5-nitro-2-carboxythienyl)-beta-alanine, m.p. 159°-160° C. (Compound 7);
N-(5-nitro-2-carboxythienyl)-gamma-amino-butyric acid, m.p. 110° C. (dec.) (Compound 8);
5-nitro-2-carboxythiophene-morpholinamide, m.p. 141°-143° C. (Compound 9);
5-nitro-2-carboxythiophene-N-methyl-piperazinamide, m.p. 136°-138° C. (Compound 10).

EXAMPLE 3

5-nitro-2-(N-acetyl)-thienylamine (Compound 11)

2-thienylamine (11.3 g; 0.1 mol) is added to 30 ml of acetic anhydride cooled to 5° C.

The reaction mixture is stirred for 60 minutes and 9 ml of fuming nitric acid (d=1.49 g/ml) are then added slowly.

The mixture is allowed to stand for 20', poured into water and extracted with ethyl ether. The organic layer is dried over sodium sulfate and the solvent is evaporated.

EXAMPLE 4

Ethyl-2-(N-(5-nitro-2-thienylamine))-methyl-ketone (Compound 14)

5-nitro-2-thienylamine (3.2 g; 0.02 mol) is dissolved in 20 ml of ethyl alcohol.

To this solution are added 20 ml of a solution of methyl-vinyl-ketone (1.5 g; 0.02 mol) in methyl alcohol.

The solution is allowed to stand overnight.

The solvent is evaporated and the residue is taken up with alcoholic hydrochloric acid.

The product is then crystallized from ethyl alcohol as hydrochloride, m.p. 141°-144° C.

EXAMPLE 5

Ethyl-2-(N-(5-nitro-2-thienylamine))-phenyl-sulfone 5-nitro-2-thienylamine (3.2 g; 0.02 mol) is dissolved in 20 ml of methanol. To this solution is added phenyl-vinyl-sulfone (3.4 g; 0.02 mol) in 20 ml of methanol.

The solution is allowed to stand overnight and acidified with alcoholic hydrochloric acid.

The product is then crystallized from ethyl as hydrochloride, m.p. 133°-135° C.

EXAMPLE 6

5-bromo-2-thiophenaldoxime (Compound 13)

5-bromo-2-thiophenaldehyde (3.8 g; 0.02 mol) is dissolved in hot methyl alcohol.

A solution of hydroxylamine hydrochloride (1.93 g; 0.11 mol) in methyl alcohol is added. The solution is allowed to stand overnight and diluted with water; the precipitate is collected by filtration; m.p. 147° C.

EXAMPLE 7

5-nitro-3-thiophenemalonic acid (Compound 12)

A mixture of thiophene-3-malonic acid (3.7 g; 0.02 mol) in 15 ml of acetic anhydride is cooled to 5° C. on a water/ice bath.

1.7 ml of fuming nitric acid (d=1.49 g/ml) is added dropwise slowly. The reaction mixture is allowed to stand for 20′. The reaction mixture is poured into water and extracted with ethyl ether. The organic layer is dried over sodium sulfate and the solvent is evaporated. The residue is crystallized from a little ethyl acetate, m.p. 127°–130° C.

What is claimed is:

1. A method for radiosensitizing cells which comprises administering to a patient in need thereof a radiosensitizing effective amount of a composition containing as an active ingredient a compound of the formula

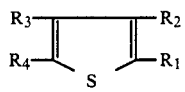

wherein $R_1$ is hydrogen, p-nitrophenoxy, halogen, carboxy, $CON(R_5, R_6)$, $CONH(CHR_9)_n$—COOH, $CH_2NHR_8$, $NH(CHR_9)_nAR_{10}$, $CH=NOH$, $NO_2$, CHO, $OR_7$, and wherein $R_5$ and $R_6$ are the same or different, and represent hydrogen, a straight or branched alkyl having 1–8C atoms, a heterocyclic ring selected from the group comprising thiophene and imidazole, ascorbyl, peptidyl having up to 5 amino acids or a sugar radical; or $R_5$ and $R_6$, together with the nitrogen atom to which they are linked, are groups necessary for forming a 5-membered heterocyclic ring which may contain other heteroatoms selected from the group consisting of O and N; $R_7$ has the meaning indicated for $R_5$ and $R_6$ above; $R_8$ is an acyl of an aliphatic carboxylic acid having 1–4C atoms; $R_9$ is hydrogen or methyl; $R_{10}$ is methyl or phenyl; n is 1, 2, 3 or 4; and A is CO or $SO_2$;

$R_2$ is hydrogen, $NO_2$, halogen, $CH(COOH)_2$, OH, $(CH_2)_nCOOH$ wheren n is 0, 1, 2, 3 or 4;

$R_3$ is hydrogen, $NO_2$, OH:

$R_4$ is hydrogen, $NO_2$, halogen, $SO_2CH_3$, OH, $N(R_5, R_6)$ wherein $R_5$ and $R_6$ have the meaning above, provided however that at least two of the substituents $R_1$, $R_2$, $R_3$ and $R_4$ are not hydrogen;

or an addition salt thereof with pharmaceutically acceptable acids or bases, together with a pharmaceutically acceptable diluent.

2. The method for radiosensitizing cells according to claim 1, wherein $R_1$ is H, bromine, iodine, carboxy, p-nitrophenoxy, $CON(R_5, R_6)$, $CONH(CHR_9)_n$—COOH, $NH(CHR_9)_nAR_{10}$, $CH=NOH$ wherein $R_5$ and $R_6$ are the same or different, and represent hydrogen, a straight or branched alkyl having 1–3C atoms, or together with the nitrogen atom to which they are linked, are the groups necessary to complete a morpholine or a piperazine ring; $R_9$ is hydrogen or methyl; $R_{10}$ is methyl or phenyl; n is 1, 2 or 3; and A is CO or $SO_2$;

$R_2$ is hydrogen, nitro, carboxy or $CH(COOH)_2$;

$R_3$ is hydrogen or nitro; and $R_4$ is hydrogen, bromine, iodine, nitro or $SO_2CH_3$.

3. A method for blocking the reaction of oxygen radicals in cells which comprises administering to a patient in need thereof an oxygen blocking effective amount of a composition containing as the active ingredient thereof a compound of the formula

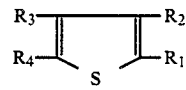

wherein $R_1$ is hydrogen, p-nitrophenoxy, halogen, carboxy, $CON(R_5, R_6)$, $CONH(CHR_9)_n$—COOH, $CH_2NHR_8$, $NH(CHR_9)_nAR_{10}$, $CH=NOH$, $NO_2$, CHO, $OR_7$, wherein $R_5$ and $R_6$ are the same or different, and respresent hydrogen, a straight or branched alkyl having 1–8C atoms, a heterocyclic ring selected from the group comprising thiophene and imidazole, ascorbyl, peptidyl having up to 5 amino acids or a sugar radical; or $R_5$ and $R_6$, together with the nitrogen atom to which they are linked, are the groups necessary for forming a 5-membered heterocyclic ring which may contain other heteroatoms selected from the group consisting of O and N; $R_7$ has the meanings indicated for $R_5$ and $R_6$ above; $R_8$ is an acyl of an aliphatic carboxylic acid having 1–4C atoms; $R_9$ is hydrogen or methyl; $R_{10}$ is methyl or phenyl; n is 1, 2, 3 or 4; and A is CO or $SO_2$;

$R_2$ is hydrogen, $NO_2$, halogen, $CH(COOH)_2$, OH, $(CH_2)_nCOOH$ wherein n is 0, 1, 2, 3 or 4;

$R_3$ is hydrogen, $NO_2$, OH;

$R_4$ is hydrogen, $NO_2$, halogen, $SO_2CH_3$, OH, $N(R_5, R_6)$ wherein $R_5$ and $R_6$ have the meaning indicated above, provided however that at least two of the substituents $R_1$, $R_2$, $R_3$ and $R_4$ are not hydrogen;

or an addition salt thereof with pharmaceutically acceptable acids or bases, together with a pharmaceutically acceptable diluent.

4. The method for blocking the reaction of oxygen radicals in cells according to claim 3 wherein $R_1$ is H, bromine, iodine, carboxy, p-nitrophenoxy, $CON(R_5, R_6)$, $CONH(CHR_9)_n$—COOH, $NH(CHR_9)_nAR_{10}$, $CH=NOH$ wherein $R_5$ and $R_6$, are the same or different, and represent hydrogen, a straight or branched alkyl having 1–3C atoms, or together with the nitrogen atom to which they are linked, are the groups necessary to complete a morpholine or a piperazine ring; $R_9$ is hydrogen or methyl; $R_{10}$ is methyl or phenyl; n is 1, 2 or 3; and A is CO or $SO_2$;

$R_2$ is hydrogen, nitro, carboxy, or $CH(COOH)_2$;

$R_3$ is hydrogen or nitro; and $R_4$ is hydrogen, bromine, iodine, nitro or $SO_2CH_3$.

* * * * *